United States Patent
Kirsch et al.

(10) Patent No.: US 9,414,967 B2
(45) Date of Patent: Aug. 16, 2016

(54) COMPOSITION, PREPARATION, AND USE OF CHITOSAN SHARDS FOR BIOMEDICAL APPLICATIONS

(71) Applicants: Loma Linda University, Loma Linda, CA (US); Loma Linda University Medical Center, Loma Linda, CA (US); North Carolina State University, Raleigh, NC (US)

(72) Inventors: Wolff M. Kirsch, Redlands, CA (US); Samuel M. Hudson, Raleigh, NC (US); Andrew Crofton, Loma Linda, CA (US)

(73) Assignees: Loma Linda University, Loma Linda, CA (US); Loma Linda University Medical Center, Loma Linda, CA (US); North Carolina State University, Raleigh, NC (US)

( * ) Notice: Subject to any disclaimer, the term of this patent is extended or adjusted under 35 U.S.C. 154(b) by 0 days.

(21) Appl. No.: 14/991,331

(22) Filed: Jan. 8, 2016

(65) Prior Publication Data

US 2016/0121021 A1 May 5, 2016

Related U.S. Application Data

(63) Continuation of application No. 14/254,827, filed on Apr. 16, 2014, now Pat. No. 9,259,357.

(51) Int. Cl.
*A61L 2/14* (2006.01)
*B29C 43/00* (2006.01)
(Continued)

(52) U.S. Cl.
CPC ..... *A61F 13/00987* (2013.01); *A61F 13/00012* (2013.01); *A61L 24/0015* (2013.01); *A61L 24/0042* (2013.01); *A61L 24/08* (2013.01); *B29C 43/003* (2013.01); *A61F 2013/00106* (2013.01); *A61L 2300/232* (2013.01);
(Continued)

(58) Field of Classification Search
USPC ........... 264/118, 140, 157, 319, 483, 488
See application file for complete search history.

(56) References Cited

U.S. PATENT DOCUMENTS 3,390,681 A 7/1968 Kurtz
3,533,940 A 10/1970 Peniston et al.
(Continued)

FOREIGN PATENT DOCUMENTS

CA 2901948 2/2014
CA 2530032 11/2015
(Continued)

OTHER PUBLICATIONS

U.S. Appl. No. 10/868,202, filed Jun. 14, 2004, Zhu et al.
U.S. Appl. No. 14/933,400, filed Nov. 5, 2015, Kirsch et al.
Bajaj G, Van Alstine WG, Yeo Y. Zwitterionic chitosan derivative, a new biocompatible pharmaceutical excipient, prevents endotoxin-mediated cytokine release. PLoS One. 2012;7(1):e30899. Epub Feb. 1, 2012. doi: 10.1371/journal.pone.0030899 [doi] PONE-D-11-17093 [pii]. PubMed PMID: 22292072; PubMed Central PMCID: PMC3265529.
(Continued)

*Primary Examiner* — Atul P. Khare
(74) *Attorney, Agent, or Firm* — Knobbe, Martens, Olson & Bear, LLP

(57) ABSTRACT

A thin chitosan-based material can be used for biomedical applications. The chitosan has been treated in a nitrogen field by applying energy to ionize nitrogen in and around the chitosan material. A single or multiple such treatments may be employed. For example, the chitosan material may be irradiated under nitrogen using γ-irradiation, treated under a nitrogen plasma, or both. A thin chitosan material can be readily treated by surface modifying treatments such as irradiating under nitrogen using γ-irradiation, treating under a nitrogen plasma, or both.

14 Claims, 10 Drawing Sheets

(51) Int. Cl.
  *A61F 13/00* (2006.01)
  *A61L 24/08* (2006.01)
  *A61L 24/00* (2006.01)
  *B29L 31/00* (2006.01)
  *B29C 43/56* (2006.01)

(52) U.S. Cl.
  CPC ....... *A61L 2300/404* (2013.01); *A61L 2400/04* (2013.01); *A61L 2400/18* (2013.01); *B29C 2043/561* (2013.01); *B29C 2793/009* (2013.01); *B29K 2005/00* (2013.01); *B29L 2031/7722* (2013.01)

(56) References Cited

U.S. PATENT DOCUMENTS

| | | | |
|---|---|---|---|
| 4,321,232 | A | 3/1982 | Bithell |
| 4,394,373 | A | 7/1983 | Malette |
| 4,452,785 | A | 6/1984 | Malette |
| 4,532,134 | A | 7/1985 | Malette et al. |
| 5,120,546 | A | 6/1992 | Hansen et al. |
| 5,413,760 | A | 5/1995 | Campbell et al. |
| 5,549,908 | A | 8/1996 | Smith et al. |
| 5,836,970 | A | 11/1998 | Pandit |
| 5,885,609 | A | 3/1999 | Amiji |
| 6,060,461 | A | 5/2000 | Drake |
| 6,465,626 | B1 | 10/2002 | Watts et al. |
| 6,565,579 | B2 | 5/2003 | Kirsch et al. |
| 6,596,296 | B1 | 7/2003 | Nelson et al. |
| 6,806,260 | B1 | 10/2004 | Hirofumi et al. |
| 7,098,194 | B2 | 8/2006 | Chenite et al. |
| 7,241,736 | B2 | 7/2007 | Hunter et al. |
| 7,252,837 | B2 | 8/2007 | Guo et al. |
| 7,371,403 | B2 | 5/2008 | McCarthy et al. |
| 7,482,503 | B2 | 1/2009 | Gregory et al. |
| 7,780,699 | B2 | 8/2010 | Zhu et al. |
| 8,012,167 | B2 | 9/2011 | Zhu et al. |
| 8,088,145 | B2 | 1/2012 | Zhu et al. |
| 8,460,708 | B2 | 6/2013 | Daniloff et al. |
| 8,513,217 | B2 | 8/2013 | Chen et al. |
| 8,536,230 | B2 | 9/2013 | Laurencin et al. |
| 8,551,501 | B2 | 10/2013 | Strong |
| 8,623,274 | B2 | 1/2014 | Kirsch et al. |
| 8,703,176 | B2 | 4/2014 | Zhu et al. |
| 8,715,719 | B2 | 5/2014 | Roorda et al. |
| 8,791,069 | B1 | 7/2014 | Sung et al. |
| 8,815,832 | B2 | 8/2014 | Wang et al. |
| 8,932,521 | B2 | 1/2015 | Kirsch et al. |
| 8,975,387 | B1 | 3/2015 | Venditti et al. |
| 9,119,894 | B2 | 9/2015 | Huang et al. |
| 9,226,988 | B2 | 1/2016 | Kirsch et al. |
| 9,259,357 | B2 * | 2/2016 | Kirsch ................. B29C 43/003 |
| 2002/0089080 | A1 | 7/2002 | Kim et al. |
| 2002/0197302 | A1 | 12/2002 | Cochrum et al. |
| 2003/0044380 | A1 | 3/2003 | Zhu et al. |
| 2003/0206958 | A1 | 11/2003 | Cattaneo et al. |
| 2005/0038369 | A1 | 2/2005 | Gregory et al. |
| 2005/0058721 | A1 | 3/2005 | Hursey |
| 2005/0118238 | A1 | 6/2005 | Zhu et al. |
| 2005/0123588 | A1 | 6/2005 | Zhu et al. |
| 2005/0177103 | A1 | 8/2005 | Hunter et al. |
| 2005/0182463 | A1 | 8/2005 | Hunter et al. |
| 2005/0260669 | A1 | 11/2005 | Kirsch et al. |
| 2006/0141060 | A1 | 6/2006 | Hursey |
| 2006/0240064 | A9 | 10/2006 | Hunter et al. |
| 2006/0293509 | A1 | 12/2006 | Hung et al. |
| 2007/0254835 | A1 | 11/2007 | Lyons et al. |
| 2008/0064998 | A1 | 3/2008 | Gregory et al. |
| 2008/0085300 | A1 | 4/2008 | Huey et al. |
| 2008/0146984 | A1 | 6/2008 | Campbell et al. |
| 2008/0160078 | A1 | 7/2008 | Chen et al. |
| 2008/0200645 | A1 | 8/2008 | Kotwal et al. |
| 2008/0241229 | A1 | 10/2008 | Li et al. |
| 2008/0248508 | A1 | 10/2008 | Baker et al. |
| 2008/0292625 | A1 | 11/2008 | Schroeter et al. |
| 2008/0302725 | A1 | 12/2008 | Feng et al. |
| 2008/0317732 | A1 | 12/2008 | Hersh et al. |
| 2009/0018479 | A1 | 1/2009 | McCarthy et al. |
| 2009/0117213 | A1 | 5/2009 | Beaulieu et al. |
| 2009/0137526 | A1 | 5/2009 | Jubert |
| 2010/0303784 | A1 | 12/2010 | Kiliaan et al. |
| 2011/0015136 | A1 | 1/2011 | Kumar-Singh et al. |
| 2011/0020337 | A1 | 1/2011 | Schwaeble et al. |
| 2011/0160851 | A1 | 6/2011 | Mueller-Lierheim |
| 2011/0306068 | A1 | 12/2011 | Miller et al. |
| 2013/0012857 | A1 | 1/2013 | Flynn et al. |
| 2013/0210761 | A1 | 8/2013 | Baker et al. |
| 2013/0216592 | A1 | 8/2013 | Delair et al. |
| 2013/0230496 | A1 | 9/2013 | Mohapatra et al. |
| 2013/0237498 | A1 | 9/2013 | Bitterman et al. |
| 2013/0244953 | A1 | 9/2013 | Xu |
| 2013/0244974 | A1 | 9/2013 | Athanasiadis et al. |
| 2013/0266549 | A1 | 10/2013 | Chenite et al. |
| 2013/0273235 | A1 | 10/2013 | Huang et al. |
| 2013/0274225 | A1 | 10/2013 | Adelman |
| 2014/0178446 | A1 | 6/2014 | Zhu et al. |
| 2015/0297674 | A1 | 10/2015 | Kirsch et al. |
| 2015/0297783 | A1 | 10/2015 | Kirsch et al. |
| 2015/0353623 | A1 | 12/2015 | Kirsch et al. |
| 2016/0082037 | A1 * | 3/2016 | Kirsch ................. A61K 31/722 514/55 |

FOREIGN PATENT DOCUMENTS

| | | |
|---|---|---|
| CN | 1833732 | 9/2006 |
| EP | 1 152 013 | 11/2001 |
| EP | 2643057 | 10/2013 |
| GB | 2095995 | 10/1982 |
| GB | 2129300 | 5/1984 |
| IN | 265561 | 3/2015 |
| KR | 20010079260 A | 9/2001 |
| KR | 20010096018 A | 11/2001 |
| MX | 2014008702 | 4/2015 |
| WO | WO 01/24840 | 4/2001 |
| WO | WO 01/41820 | 6/2001 |
| WO | WO 02/102276 | 12/2002 |
| WO | WO 2005/041811 | 5/2005 |
| WO | WO 2007/044510 | 4/2007 |
| WO | WO 2007/074327 | 7/2007 |
| WO | WO 2009/011856 | 1/2009 |
| WO | WO 2011/050476 | 5/2011 |
| WO | WO 2011/066471 | 6/2011 |
| WO | WO 2013/123426 | 8/2013 |
| WO | WO 2013/138368 | 9/2013 |
| WO | WO 2013/140190 | 9/2013 |
| WO | WO 2013/150193 | 10/2013 |
| WO | WO 2015/021303 | 2/2015 |
| WO | WO 2015/123501 | 8/2015 |
| WO | WO 2015/123778 | 8/2015 |
| WO | WO 2015/160719 | 12/2015 |
| WO | WO 2015/195580 | 12/2015 |

OTHER PUBLICATIONS

Bernie, J.E., et al.: "Evaluation of Hydrogel Tissue Sealant in Porcine Laparoscopic Partial-Nephrectomy Model," J Endourol. 2005;19(9):1122-6. Epub Nov. 15, 2005. doi: 10.1089/end.2005.19. 1122 [doi]. PubMed PMID: 16283851.

Campion, R.P.: "The Influence of Structure on Autohesion (Self-Tack) and other forms of Diffusion into Polymers," J Adhesion. 1975;7:1-23.

Chakrabarti M, Cheng KT, Spicer KM, Kirsch WM, Fowler SD, Kelln W, et al. Biodistribution and radioimmunopharmacokinetics of 131I-Ama monoclonal antibody in atherosclerotic rabbits. Nucl Med Biol. 1995;22(6):693-7. Epub Aug. 1, 1995. doi: 096980519500008L [pii]. PubMed PMID: 8535329.

Chou, T.C., et al.: Chitosan enhances platelet adhesion and aggregation, Biochem Biophys Res Commun. 2003;302(3):480-3. Epub Mar. 5, 2003. doi: S0006291X03001736 [pii]. PubMed PMID: 12615058.

Cooper et al.: "Reducing Pyrogens in Cleanroom Wiping Materials," Pharmaceutical Engineering, Jul./Aug. 1996 vol. 16, No. 4.

(56) References Cited

OTHER PUBLICATIONS

Cooper, J.F., "Resolving LAL Test Interferences," J Parenter Sci Technol. 1990;44(1):13-5. . Epub Jan. 1, 1990. PubMed PMID: 2313485.

Davis KW, Strawderman WE, Whitby JL. The rationale and a computer evaluation of a gamma irradiation sterilization dose determination method for medical devices using a substerilization incremental dose sterility test protocol. J Appl Bacteriol. 1984;57(1):31-50. Epub Aug. 1, 1984. PubMed PMID: 6490563.

Davydova, et al.: Interaction of bacterial endotoxins with chitosan. Effect of endotoxin structure, chitosan molecular mass, and ionic strength of the solution on the formation of the complex, Sep. 2000, 1 page.

Diesen, D.L., et al.: "Bovine Thrombin: History, Use, and Risk in the Surgical Patient," Vascular. 2008;16 Suppl 1:S29-36. Epub Mar. 1, 2008. PubMed PMID: 18544303.

Dutkiewicz, J.K.: "Superabsorbent Materials from Shellfish Waste—A Review," J Biomed Mater Res. 2002;63(3):373-81.

Gee AP, Sumstad D, Stanson J, Watson P, Proctor J, Kadidlo D, et al. A multicenter comparison study between the Endosafe PTS rapid-release testing system and traditional methods for detecting endotoxin in cell-therapy products. Cytotherapy. 2008;10(4):427-35. Epub Jun. 25, 2008. doi: 792790253 [pii] 10.1080/14653240802075476 [doi]. PubMed PMID: 18574775; PubMed Central PMCID: PMC2518960.

Gryczka et al.: "The mechanism of chitosan degradation by gamma and e-beam irradiation", 2008, 1 page, 170.

Guyomard, et al.: "Defining of the pyrogenic assurance level (PAL) of irradiated medical devices", Jun. 1987, 2 pages.

Guyomard, et al.: "Effects of Ionizing Radiations on Bacterial Endotoxins: Comparison Between Gamma Radiations and Accelerated Electrons", 6 pages.

Guzzo, T.J., et al.: "Safety and Efficacy of a Surgeon-Prepared Gelatin Hemostatic Agent Compared with FloSeal for Hemostasis in Laparoscopic Partial Nephrectomy," J Endourol. 2009;23(2):279-82.

Gyorgy, et al.: "Modification of the Chemical Composition and Structure of the U.S. Reference Standard Endotoxin (RSE) by Co Radiation", 1986, 13 pages.

Gyorgy, et al.: The Concentration , Physical State, and Purity of Bacterial Endotoxin Affect its Detoxification by Ionizing Radiation, 1986, 9 pages.

Heffernan MJ, Zaharoff DA, Fallon JK, Schlom J, Greiner JW. In vivo efficacy of a chitosan/IL-12 adjuvant system for protein-based vaccines. Biomaterials. 2011;32(3):926-32. Epub Oct. 23, 2010. doi: S0142-9612(10)01255-X [pii] 10.1016/j.biomaterials.2010.09.058 [doi]. PubMed PMID: 20965561; PubMed Central PMCID: PMC2992965.

Helfand, E., et al.: "Theory of the Interface Between Immiscible Polymers," J Chem Phys. 1972;57:1812-3.

Hobday, C.D., et al.: "Postoperative Small Bowel Obstruction Associated with Use of Hemostatic Agent," J Min Invas Gynecol. 2009;16(2):224-6.

Incorporated JP. Thrombin-JMI package insert. Bristol, VA 2005.

Jimenez-Castellanos, R., et al.: "Mucoadhesive Drug Delivery Systems," Drug Dev Ind Pharm. 1993;19:143-94.

Johnston, W.K., et al.: "Acute Integrity of Closure of Partial Nephrectomy: Comparison of 7 Agents in a Hypertensive Porcine Model," J Urol. 2006;175(6):2307-11.

Kenawy, E.R., et al.: "Biologically Active Polymers: Modification and Anti-microbial Activity of Chitosan Derivatives," J Bioactive Compative Polymers. 2005;20:95-111.

Kind, G.M., et al.: "Chitosan: Evaluation of a New Hemostatic Agent," Curr Surg. 1990;47(1):37-9.

Kong MG, Kroesen G, Morfill G, Nosenko T, Shimizu T, van Dijk J, et al. Plasma medicine: an introductory review. New J Phys. 2009;11(11).

Kvam E, Davis B, Mondello F, Garner AL. Nonthermal atmospheric plasma rapidly disinfects multidrug-resistant microbes by inducing cell surface damage. Antimicrob Agents Chemother. 2012;56(4):2028-36. Epub Jan. 11, 2012. doi: AAC.05642-11 [pii] 10.1128/AAC.05642-11 [doi]. PubMed PMID: 22232292; PubMed Central PMCID: PMC3318311.

Laroussi M. Low temperature plasma-based sterilization: Overview and state-of-the-art. Plasma Process Polym. 2005;2:391-400. doi: 10.1002/ppap.200400078.

Lawson, J. H., et al.: "Antihuman Factor V Antibodies After Use of Relatively Pure Bovine Thrombin," Ann Thorac Surg. 2005;79(3):103 7-8.

Lieder R, Gaware VS, Thormodsson F, Einarsson JM, Ng CH, Gislason J, et al. Endotoxins affect bioactivity of chitosan derivatives in cultures of bone marrow-derived human mesenchymal stem cells. Acta Biomater. 2013;9(1):4771-8. Epub Sep. 6, 2012. doi: S1742-7061(12)00419-9 [pii] 10.1016/j.actbio.2012.08.043 [doi]. PubMed PMID: 22947323.

Louie, M.K., et al.: "Laparoscopic partial nephrectomy: six degrees of haemostasis," BJU Int. 2011;107(9):1454-9.

Low M, Van Buskirk JJ, Kirsch WM. Detection of gamma carboxyglutamic acid by dansylation. . In: Suttie JW, editor. Vitamin K Metabolism: Vitamin K-Dependent Proteins. Baltimore: University Park Press; 1979. p. 150-2.

Luna SM, Silva SS, Gomes ME, Mano JF, Reis RL. Cell adhesion and proliferation onto chitosan-based membranes treated by plasma surface modification. J Biomater Appl. 2011;26(1):101-16. Epub Jun. 1, 2010. doi: 0885328210362924 [pii] 10.1177/0885328210362924 [doi]. PubMed PMID: 20511386.

Margulis, V., et al.: "Application of Novel Hemostatic Agent During Laparoscopic Partial Nephrectomy," J Urol. 2005;174(2):761-4.

Mazzotti, F., et al.: "In vitro pyrogen test—A new test method for solid medical devices," J Biomed Mater Res A. 2007;80(2)276-82.

Messerer P, Halfmann H, Czichy M, Schulze M, Awakowicz P. "Plasma sterilization and surface modification of thermolabile materials", TMS (The Minerals, Metals & Materials Society). 2005;2005:205-15.

Morent, R., et al.: "Non-thermal plasma treatment of textiles," Surface & Coatings Technology 2008;202:3427-49.

Morfill GE, Kong MG, Zimmerman JL. Focus on plasma medicine. New J Phys. 2009;11(11).

Mosian et al.: Low-temperature sterilization using gas plasmas: a review of the experiments and an analysis of the inactivation mechanisms, Jul. 1000, 21 pages.

Naberezhnykh, et al.: Interaction of chitosans and their N-acylated derivatives with lipopolysaccharide of gram-negative bacteria, Apr. 2008, 1 page.

Navai, N., et al.: "Why Not Partial Nephrectomy?," Urology 72: 243-246, 2008.

Ortel, T.L., et al.: "Immunologic Impact and Clinical Outcomes After Surgical Exposure to Bovine Thrombin," Ann surg. 2001;233(1):88-96.

Pace G, Saldutto P, Vicentini C, Miano L. Haemostatics in surgery and our experience in the enucleoresection of renal cell carcinoma. World J Surg Onc. 2010;8(37):1-6.

Park, E.L., et al.: "Evaluation of Polyethylene Glycol Based Hydrogel for Tissue Sealing After Laparoscopic Partial Nephrectomy in a Porcine Model," J Urol. 2004;172(6 Pt 1):2446-550.

Pattaras, J.G., et al.: "Incidence of Postoperative Adhesion Formation After Transperitoneal Genitourinary Laparoscopic Surgery," Urology. 2002;59(1):37-41.

Peppas, N.A., et al.: "A theory of molecular diffusion in the intestinal mucas," J Pharm. 1984;20:107-18.

Perola, et al.: "Methods of Endotoxin Removal from Biological Preparations: a Review", 2007, 16 pages.

Prior, J.J., et al.: "A Sprayable Hemostat Containing Fibrillar Collagen, Bovine Thrombin, and Autologous Plasma," Ann Thorac Surg. 1999;68(2):479-85.

Pruthi, R.S., et al.: "The use of a fibrin tissue sealant during laparoscopic partial nephrectomy," BJU Int. 2004;93(6):813-7.

Ramanathan, R., et al.: "A Review of Methods for Hemostatis and Renorrhaphy After Laparoscopic and Robot-assisted Laparoscopic Partial Nephrectomy," Curr Urol Rep. 2010;11(3):208-20.

(56) References Cited

OTHER PUBLICATIONS

Rane, A., et al.: "Evaluation of a Hemostatic Sponge (TachoSil®) for Sealing of the Renal Collecting System in a Porcine Laparoscopic Partial Nephrectomy Survival Model," J Endourol. 2010;24(4):599-603.

Rao, S.B. et al.: "Use of chitosan as a biomaterial: Studies on its safety and hemostatic potential," J Biomed Mater Res. 1997;34(1):21-8.

Rathke, T.D., et al.: "Review of Citin and Chitosan as Fiber and Film Formers," JMS-Rev Macromol chem Phys. 1994;C34(3):375-437.

Reid, "Gamma Processing Technology: An Alternative Technology for Terminal Sterilization of Parenterals", 14 pages.

Rossi F, Kylian O, Rauscher H, Hasiwa M, D. G. Low pressure plasma discharges for the sterilization and decontamination of surfaces. New J Phys. 2009;11(11).

Roth S, Feichtinger J, Hertel C. Characterization of Bacillus subtilis spore inactivation in low-pressure, low-temperature gas plasma sterilization processes. J Appl Microbiol. 2010;108(2):521-31. Epub Aug. 8, 2009. doi: JAM4453 [pii] 10.1111/j.1365-2672.2009.04453.x [doi]. PubMed PMID: 19659696.

Salmon, S., et al.: "Shear-Precipitated Chitosan Powders, Fibrids, and Fibrid Papers: Observations on their Formation and Characterization," J Polym Sci Part B: Polym Phys. 1995;33(Part B):1007-14.

Sands, J.J., et al.: "Antibodies to Topical bovine Thrombin Correlate With Access Thrombosis," Am J Kidney Dis. 2000;35(5):796-801.

Sarfati, M.R., et al.: "Severe Coagulopathy following Intraoperative Use of Topical Thrombin," Ann vasc Surg. 2004;18(3):349-51.

Savage, W.J., et al.: "Acquired Coagulation Factor Inhibitors in Children Afer Topica Bovine Thrombin Exposure," Pediatr Blood Cancer. 2007;49(7):1025-9.

Schoenecker JG, Hauck RK, Mercer MC, Parker W, Lawson JH. Exposure to topical bovine thrombin during surgery elicits a response against the xenogeneic carbohydrate galactose alphal-3galactose. J Clin Immunol. 2000;20(6):434-44. Epub Feb. 24, 2001. PubMed PMID: 11202233.

Seyednejad, H., et al.: Topical haemostatic agents, Br J Surg. 2008;95(10):1197-225.

Shintani, et al.: Inactivation of Microorganisms and Endotoxins by Low Temperature Nitrogen Gas Plasma Exposure, Mar. 2007, 13 pages.

Shintani, H.: "Inactivation of Prion and Entotoxins by Nitrogen Gas Plasma Exposure," Pharmaceut Anal Acta. 2012;3(8):1-4.

Shobita et al.: "Radiation Processed Chitosan A Potent Antioxidant", Oct. 2006, 6 pages.

Silva, S.S., et al.: "Plasma Surface Modification of Chitosan Membranes: Characterization and Preliminary Cell Response Studies," Macromol Biosci. 2008;8(6):568-76.

Streiff, M.B., et al.: "Acquired FV inhibitors: a needless iatrogenic complication of bovine thrombin exposure," Transfusion. 2002;42(1)18-26.

Subar, P.: "Chitosan: The Hemostatic Agent," Denistry. 1992;12(3):18-9, 22.

Tabuchi K, Kirsch WM. Immunocytochemical localization of S-100 protein in neurons and glia of hamster cerebellum. Brain Res. 1975;92(1):175-80. Epub Jul. 4, 1975. doi: 0006-8993(75)90541-7 [pii]. PubMed PMID: 809095.

Tabuchi K, Lehman JM, Kirsch WM. Immunocytochemical localization of simian virus 40 T antigen with peroxidase-labeled antibody fragments. J Virol. 1976;17(2):668-71. Epub Feb. 1, 1976. PubMed PMID: 176435; PubMed Central PMCID: PMC515456.

Uribe, C.A., et al.: "What Happends to Hemostatic Agents in Contact with Urine? An in Vitro Study," J Endourol. 2005;19(3):312-7.

Wake, W.C.: "Theories of Adhesion and Adhesive Action," Adhesion and the Formulation of Adhesives, Second Edition, 1982:67-199.

Wedmore I, McManus JG, Pusateri AE, Holcomb JB. A special report on the chitosan-based hemostatic dressing: experience in current combat operations. J Trauma. 2006;60(3):655-8.

Winterbottom N, Kuo JM, Nguyen K, Reich CJ, Trent KJ, Rondinone JF, et al. Antigenic responses to bovine thrombin exposure during surgery: a prospective study of 309 patients. J Applied Res. 2002;2(1):1-11.10.

Xie, H., et al.: "Chitosan Hemostic Dressing for Renal Parenchymal Wound Sealing in a Porcine Model: Implications for Laparoscopic Partial Nephrectomy Technique," JSLS. 2008; 12(1):18-24.

Zaharoff DA, Hoffman BS, Hooper HB, Benjamin CJ, Jr., Khurana KK, Hance KW, et al. Intravesical immunotherapy of superficial bladder cancer with chitosan/interleukin-12. Cancer Res. 2009;69(15):6192-9. Epub Jul. 30, 2009. doi: 0008-5472.CAN-09-1114 [pii] 10.1158/0008-5472.CAN-09-1114 [doi]. PubMed PMID: 19638573; PubMed Central PMCID: PMC2788203.

PCT Invitation to Pay Additional Fees and Partial Search Report, mailed Jul. 13, 2015.

Ahmed, et al. "Use of Microporous Polysaccharide Particles in Prolonged Vascular Access Bleeding After Hemodialysis", American Society of Nephrology, Friday, Nov. 1, 2002, Poster Board No. F-P0835.

Csako, et al.: "Modification of the Chemical Composition and Structure of the U.S. Reference Standard Endotoxin (RSE) by Co Radiation", 1986, 13 pages.

Csako, et al.: The Concentration, Physical State, and Purity of Bacterial Endotoxin Affect its Detoxification by Ionizing Radiation, 1986, 9 pages.

Drake. J. F. "Fate of Porous Starch Microbeads in Mammalian Tissues", Nov. 18, 2002.

Ereth et al., "Efficacy of Microporous Polysaccharide Hemospheres on Liver Punch biopsies in Porcine Model", Anesthesiology Abstracts of Scientific Papers Annual Meeting, No. 2003, 2003, Abstract No. A-153 URL, Abstract XP002476226 & 2003 Annual Meeting of the American Society of Anesthesiologists, San Francisco, CA, Oct. 11-15, 2003.

Everaers, et al. "Rheology and Microscopic Topology of Entangled Polymeric Liquids", Science, vol. 202, Feb. 6, 2004.

Ereth et al. "Microporous Polysaccharide Hemospheres Provide Effective Topical Hemostasis in a Human Modified Bleeding Time Inclusion Model", Medafor-Hemoostatic Polymer Technologies, Sep. 2002.

Heller et al., "Alginate/chitosan microporous microspheres for the controlled release of proteins and antigens", Proceedings of the Controlled Release Society, 19096, No. 23, pp. 269-270.

Mi et al.: "Control of wound infections using a bilayer chitosan wound dressing with sustainable antibiotic delivery", Biomed Mater Res 59: 438-449, 2002.

Pathology Report, "The Wound Healing Effects in Porcine Skin Grafts After Application of Microporous Polysaccharide Hemospheres (MPH)", Aug. 14, 2002, Medafor, Inc., Minneapolis, MN.

Tan et al., "Effectiveness of microporous polysaccharide hemospheres for achieving hemostasis in mohs micrograph surgery", Dermatologic Surgery: Official Publication for American Society for Dermatologic Surgery, Jun. 2004, vol. 30, No. 6, pp. 908-914.

Viyoch, et al. "Formulation and Development of a Patch Containing Tamarind Fruit Extract by Using the Blended Chitosan Starch as a Rate Controlling Matrix" Intl. J of Cosmetic Science, V25 p. 113, 2003.

Wang et al.: "Studies on hepatic arterial embolization with cisplatin-chitosan-microspheres in dogs" Abstract XP002476227, Medline Database Accession No. NLM8712014, Acta Pharmaceutica Sinica, Dec. 1995, vol. 30, No. 12, pp. 891-895.

Weller, et al.: Cerebral amyloid angiopathy in the aetiology and Immunotherapy of Alzheimer disease, Clinical Neurosciences, Review. Oct. 2009, pp. 1-13.

Yang, et al.: Effect of Chitosan Molecular Weight and Deacetylation Degree on Hemostasis, J. Biomed. Mat. Res. B: Appl. Biomat., 2007, pp. 131-137.

PCT International Search Report and Written Opinion, mailed Oct. 19, 2015.

* cited by examiner

COMPOSITION, PREPARATION, AND USE OF CHITOSAN SHARDS FOR BIOMEDICAL APPLICATIONS

CROSS-REFERENCE TO RELATED APPLICATIONS

This application is a continuation of and claims the benefit of U.S. application Ser. No. 14/254,827, filed Apr. 16, 2014. The disclosure of this prior application is incorporated by reference in its entirety and should be considered a part of this specification.

BACKGROUND

1. Field of the Invention

Hemostatic materials made from chitosan are provided, more particularly, chitosan shards having reduced pyrogenicity.

2. Description of the Related Art

Surgical procedures and traumatic injuries are often characterized by massive blood loss. Conventional approaches such as manual pressure, cauterization, or sutures may be time consuming and are not always effective in controlling bleeding.

Over the years, a number of topical hemostatic agents have been developed to control bleeding during surgical procedures and to control bleeding resulting from traumatic injury. Some agents such as collagen-based powders, sponges, or cloths are of a particulate nature. Particulate hemostatic agents provide a lattice for natural thrombus formation, but are unable to enhance this process in coagulopathic patients. Microfibrillar collagen, a particulate hemostatic agent, comes in powder form and stimulates the patient's intrinsic hemostatic cascade. However, this product has been reported to embolize and induce a localized inflammatory response if used during cardiopulmonary bypass. Further, particulates such as powders and even gels are difficult to control, and are easily carried away from an active bleeding site.

Pharmacologically-active agents such as thrombin can be used in combination with a particulate carrier, for example, as in a gelfoam sponge or powder soaked in thrombin. Thrombin has been used to control bleeding on diffusely bleeding surfaces, but the lack of a framework onto which the clot can adhere has limited its use. The autologous and allogenic fibrin glues can cause clot formation, but do not adhere well to wet tissue and have little impact on actively bleeding wounds.

Chitosan, the N-deacetylated derivation of chitin, has demonstrated hemostatic effectiveness as well as biocompatibility, biodegradability, and anti-bacterial activity. Chitosan has been shown to secure mucoadhesion and hemostasis despite defibrination and anticoagulation. FDA approved topical chitosan hemostats include Celox™ (a granular powder) and HemCon (a lyophilized chitosan film). Also FDA approved, for external use, is a microfibrillar high molecular weight chitosan in the form of sponge, puff or non-woven fabric.

Although chitosan has been shown to be an effective hemostat, the traditional, inexpensive methods for manufacturing commodity-grade chitosan yields a product that is laden with pyrogens, particularly endotoxins, which limit its applicability in the biological and medical arenas, as minute amounts of endotoxins may induce septic responses when contacted with mammalian tissue.

Experimental and biocompatibility artifacts are generated by unappreciated endotoxins in commercially available, "medical grade" chitosan. For example, an "ultra-pure" chitosan (PROTASAN™ S-213 frp, NovaMatrix™, a business unit of FMC BioPolymer, Sandvika, Norway) was advertised as having an endotoxin burden <100 EU/gm, a level that prohibits implantation but allows topical applications. However, an independent analysis of Protasan S-213 found endotoxin levels in the hemostat to be 247 EU/gm, over two times higher than the manufacturer's guaranteed level. Additionally, a medical-grade chitosan marketed as POLYPROLATE™ derived from Dungeness crab shells (Scion Cardio-Vascular, Inc., Miami, Fla.) has an EU level at 28 EU/gm. The FDA requires an EU level below 20 EU/gm for implantable medical devices which includes chitosan hemostats. The lack of an FDA-approved, implantable depyrogenated chitosan has halted advancements and development of promising techniques utilizing internal or implantable chitosan materials.

SUMMARY

There is a need for a chitosan-based hemostatic material having reduced levels of pyrogens, and/or one in which the endotoxins have been removed and/or inactivated sufficiently to avoid inducing septic responses when contacted with mammalian tissue. Additionally, the ability to produce chitosan substances that are more effectively depyrogenated or purified is desirable.

In accordance with one aspect, a method of making a material comprises processing chitosan into a block by a physical process, dividing the block into an ultra-thin chitosan material, and irradiating the ultra-thin chitosan material under nitrogen using γ-irradiation. In some embodiments, the method further comprising utilizing large chitosan flakes directly obtained from shellfish with multi centimeter dimensions. In some embodiments, the method further comprising plasticizing the large chitosan flakes with aqueous organic acids and compressing and consolidating under a vacuum to form the block. In some embodiments, the physical process comprises compression of the chitosan to form the block. In some embodiments, the ultra-thin chitosan material comprises chitosan shards. In some embodiments, the ultra-thin chitosan material comprises chitosan fibrids. In some embodiments, the chitosan fibrids are 0.15 mm thick and 0.5 mm wide. In some embodiments, the ultra-thin chitosan material comprises narrow strips of chitosan material. In some embodiments, the narrow strips are 1 mm wide, 0.5 mm thick, and up to 5 cm long.

In some embodiments, the method further comprises processing the ultra-thin chitosan material into a hemostatic device comprising a network of the ultra-thin chitosan material. In some embodiments, the method further comprises processing the ultra-thin chitosan material into a drug delivery device comprising a network of the ultra-thin chitosan material. In some embodiments, the method further comprises dividing the block by shredding or slitting the block. In some embodiments, the method additionally comprises treating the ultra-thin chitosan material under a nitrogen plasma. In some embodiments, the method additionally comprises soaking the ultra-thin chitosan material in an alcohol prior to treating with γ-irradiation or plasma.

In accordance with another aspect, a method of making a material comprises processing chitosan by shear induced precipitation of a chitosan solution, and producing a pulp-like ultra-thin chitosan material. In some embodiments, the method further comprises dripping a dilute solution into a stirred coagulant. In some embodiments, the chitosan solution is stirred by a shear disc.

In accordance with another aspect, an apparatus comprises a hemostatic material, the material comprising an ultra-thin material, the ultra-thin material comprising chitosan, wherein the ultra-thin material is irradiated under nitrogen using γ-irradiation. In some embodiments, the ultra-thin material is formed from compression of the chitosan into a block and subsequent shredding or slicing of the chitosan block. In some embodiments, the ultra-thin material is configured to be processed into a pad, a sheet, a puff, or a fleece. In some embodiments, the ultra-thin material is configured to be processed into a hemostatic device comprising a network of ultra-thin material. In some embodiments, the ultra-thin material is configured to be processed into a drug delivery device comprising a network of the ultra-thin material. In some embodiments, the ultra-thin material comprises chitosan shards. In some embodiments, the ultra-thin material comprises chitosan fibrids. In some embodiments, the chitosan fibrids are 0.15 mm thick and 0.5 mm wide. In some embodiments, the ultra-thin material comprises narrow strips. In some embodiments, the narrow strips are 1 mm wide, 0.5 mm thick, and up to 5 cm long. In some embodiments, the ultra-thin material is treated under a nitrogen plasma. In some embodiments, the ultra-thin material is soaked in an alcohol prior to treating with γ-irradiation or plasma.

DETAILED DESCRIPTION

Chitosan is obtained from chitin, a widely available biopolymer obtained principally from shrimp and crab shell waste. Chitosan is the main derivative of chitin, and is the collective term applied to deacetylated chitins in various stages of deacetylation and depolymerization. The chemical structure of chitin and chitosan is similar to that of cellulose. The difference is that instead of the hydroxyl group as is bonded at C-2 in each D-glucose unit of cellulose, there is an acetylated amino group (—NHCOCH$_3$) at C-2 in each D-glucose unit in chitin and an amino group at C-2 in each D-glucose unit of chitosan.

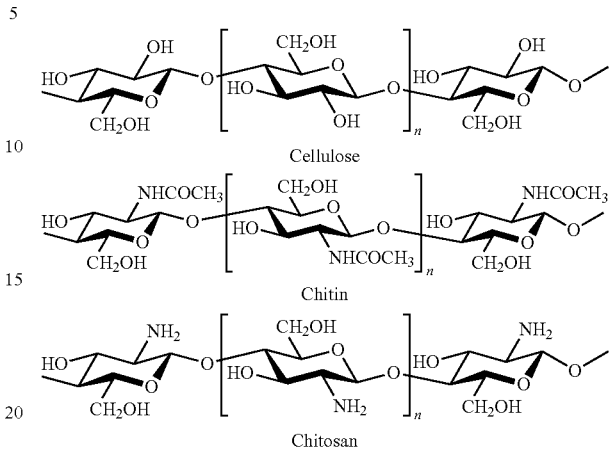

Chitin and chitosan are both nontoxic, but chitosan is used more widely in medical and pharmaceutical applications than chitin because of its good solubility in acid solution. Chitosan has good biocompatibility and is biodegradable by chitosanase, papain, cellulase, and acid protease. Chitosan exhibits anti-inflammatory and analgesic effects, and promotes hemostasis and wound healing. Chitosan has also been shown to be an effective hemostatic agent. Chitosan hemostasis is believed to be mediated by positively charged amine groups binding to negatively charged red cell and platelet surfaces forming a mucoadhesive coagulum without activation of classical coagulation pathways.

In an embodiment, a hemostatic device made from chitosan can be constructed in the form of sponge, puff or nonwoven fabric. The chitosan materials are discussed in U.S. Publ. No. 2005/0123588 A1 and U.S. Publ. No. 2005/0240137 A1. The entirety of both of these published patent applications, and particularly the disclosure directed to making and using chitosan-based hemostatic devices, is hereby incorporated by reference in its entirety. Other forms of chitosan known in the art can also be used as described herein.

As discussed above, chitosan is formed from chitin, which is present in crustacean shells as a composite with proteins and calcium salts. Chitin is produced by removing calcium carbonate and protein from these shells, and chitosan is produced by deacetylation of chitin in a strong alkali solution.

Figure 1:
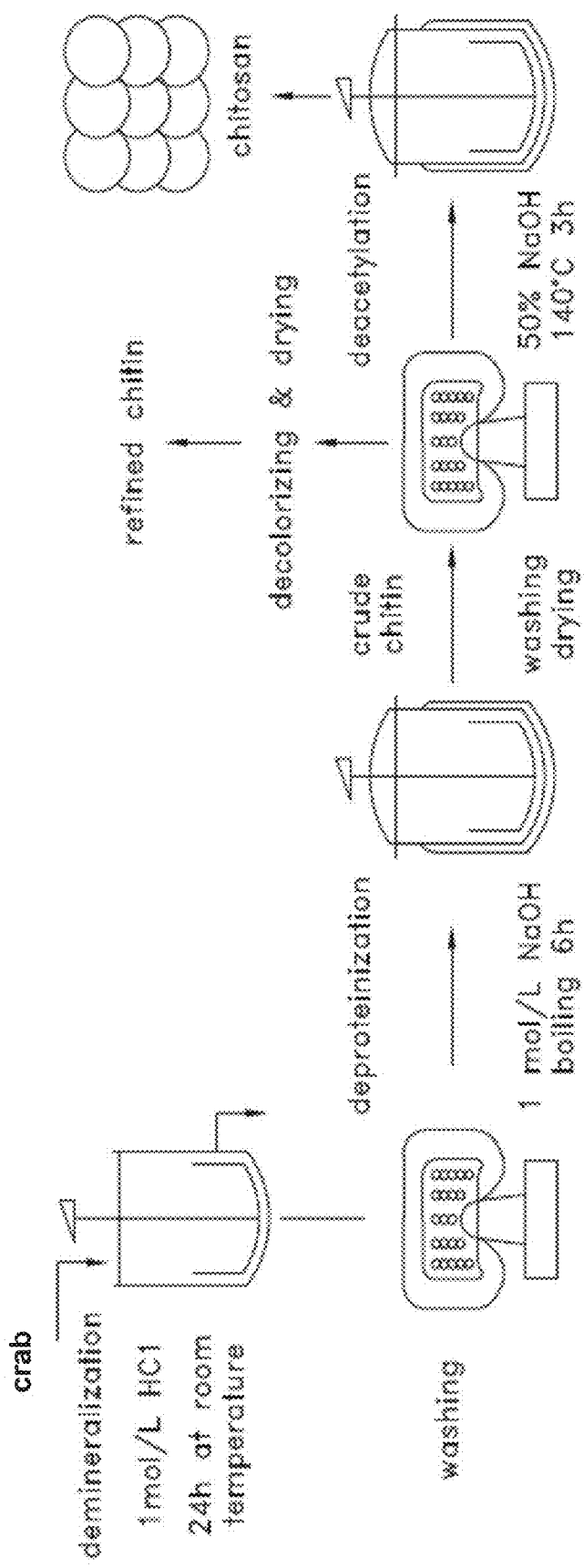
FIG. 1 schematically depicts a process for obtaining chitosan from crustacean shell waste in accordance with one embodiment.

One method for obtaining chitosan from crab, shrimp or other crustacean shells is schematically depicted in FIG. 1 and described as follows. Calcium carbonate is removed by immersing the shell in dilute hydrochloric acid at room temperature for 24 hours (demineralization). Proteins are then extracted from the decalcified shells by boiling them with dilute aqueous sodium hydroxide for six hours (deproteinization). The demineralization and deproteinization steps are preferably repeated at least two times to remove substantially all of the inorganic materials and proteins from the crustacean shells. The crude chitin thus obtained is washed then dried. The chitin is heated at 140° C. in a strong alkali solution (50 wt. %) for 3 hours. Highly deacetylated chitosan exhibiting no significant degradation of molecular chain is then obtained by intermittently washing the intermediate product in water two or more times during the alkali treatment.

Chitosan can then be formed into a fiber, flakes, shard, or other similar product that can be used to produce chitosan textiles or pads. One method of producing chitosan fibers involves a wet spinning method. In some embodiments, the chitosan can be prepared into thin films and/or chitosan shards through compression, shredding, slitting, and/or other techniques as is described in detail herein.

Normally, however, chitosan is laden with pyrogens, particularly endotoxins, which can limit its applicability in the biological and medical arenas, as minute amounts of endotoxins may induce septic responses when contacted with mammalian tissue. As such, in accordance with some embodiments, chitosan materials are used externally so as to minimize the likelihood of a septic response. In other embodiments, such chitosan materials can be used during surgeries, but only for temporary purposes, and are not implanted or left within a patient.

Endotoxins are essentially the skeletal or cellular remains and by-product secretions of dead bacteria, which are ubiquitous and found in the air, on surfaces and in food and water. More precisely, endotoxins are complex amphiphilic lipopolysaccharides (LPS) having both polysaccharide and lipophilic components. They are composed of pieces of the lipopolysaccharide wall component of Gram-negative bacteria. An example of LPS is shown below.

inactivation of endotoxins in order to make biological materials useful for medical purposes. Some of the treatment methods that have been researched and employed include heat, acid base hydrolysis, oxidation, ionizing radiation such as gamma-irradiation, and ultra filtration. These methods have varying ranges of effectiveness, expense, and suitability for particular products.

It has proven difficult, however, to develop an endotoxin removal or inactivation process (depyrogenation) that is suitable for chitosan as known processes such as contacting the chitosan with a strong base or γ-irradiating aqueous chitosan solutions tends to depolymerize the chitosan.

It has been found that high molecular weight chitosan has less of an affinity for endotoxins than low molecular weight chitosan. Thus, although a need to inactivate endotoxins likely still exists, the high molecular weight chitosan is more amenable to successful inactivation treatment.

Chitosan is graded by "purity," ranging from impure "food" or "commodity grade" to highly purified "medical grade." To qualify as "medical grade" chitosan endotoxin/pyrogen levels have to be reduced as designated by the FDA and U.S. Pharmacopeia. The endotoxin standards (USP27) for FDA approval of implantable medical devices (chitosan

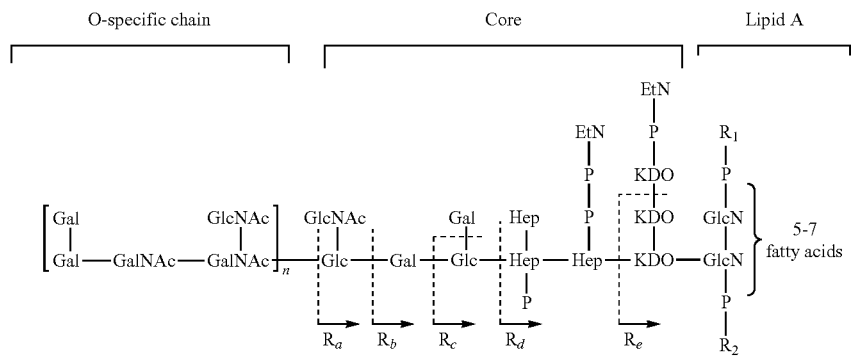

The terms endotoxin and pyrogen are often used interchangeably. Endotoxins are one of many pyrogens, which are substances that elicit a fever response in the bloodstream of a mammalian body. Vascular or lymphatic exposure to endotoxins can lead to severe sepsis, septic shock, and potential death. Thus, endotoxins are of particular concern to those manufacturing medical devices as they are one of the most potent pyrogens that can contaminate a product.

As such, pharmaceuticals, medical devices and products that contact human tissue, blood, bone or that can be absorbed by the body or implanted within the body must meet stringent levels of endotoxin control. The US Pharmacopeia has set specifications for endotoxin units (EU) for medical devices. The current standard (USP27) specifies <20 EU per device (e.g. <0.5 EU/mL in water). Preferred embodiments of chitosan-based hemostats anticipated for internal use have sufficiently reduced levels of endotoxins to comply with such standards.

Endotoxins are notoriously difficult to remove from materials. They are extremely resilient; they are strong, tough and elastic, remain viable after steam sterilization and normal desiccation, and can pass through filters. Research shows that temperatures in excess of 200° C. for up to an hour can be required to remove endotoxin contamination.

As endotoxins are ubiquitous in biological materials, much effort and research has been dedicated to removal and/or hemostats) are <20 EU (endotoxin units) per device or <0.5 EU/ml in water. Since endotoxin molecular weights vary (10,000 to $10^6$ Da), quantitation is measured as EU, where one EU is equivalent to 100 pg of E. coli lipopolysaccharide (LPS). These levels are typically measured by the Limulus Amoebocyte Lysate (LAL) test.

There is wide variation in endotoxin levels of commercially available, shellfish-sourced "medical grade" chitosan. Table 1 below shows endotoxin levels in commercially available "medical grade" chitosans. The commercially available "medical grade" chitosans as shown in Table 1 have endotoxin levels that do not meet the FDA endotoxin standards for implantable medical devices.

TABLE 1

| Sample | Endotoxin concentration EU/gm |
|---|---|
| Chitosan glutamate | 247 |
| Glycol chitosan | 311 |
| LMCS (precursor low M.W. chitosan) | 311 |
| ZWC (An/Am = 0.3) | 6,860 |
| ZWC (An/Am = 0.7) | 14,150 |

Endotoxin levels in commercially available "medical grade" chitosans
LMCS = precursor low M.W. chitosan;
ZWC, ZWC Zwitterionic chitosan Preferably, handling and storage of the manufactured chitosan product is conducted in an endotoxin-reduced, UV irradiated environment. All bags, containers, and storage materials preferably are pyrogen free and the product is stored and transferred in a nitrogen atmosphere.

The results of the use of γ-irradiation techniques in a nitrogen environment on chitosan as discussed in U.S. Pat. No. 8,623,274, the entirety of which, particularly the disclosure directed to making, using depyrogenated chitosan-based devices by the use of nitrogen plasma and gamma irradiation treatment, is hereby incorporated by reference in its entirety. In U.S. Pat. No. 8,623,274, chitosan samples were analyzed to determine whether γ-irradiation had effectively inactivated endotoxins and whether the γ-irradiation had caused depolymerization and/or otherwise damaged the chitosan fibers. It was concluded that γ-irradiation of chitosan under the conditions present in that testing effectively inactivates endotoxins. Additionally, testing of the γ-irradiated chitosan against non-irradiated chitosan for hemostatic efficacy resulted in no detectable difference. Further, the irradiated chitosan fibers were structurally intact, and maintained a high surface area that was available for interaction with blood. It was concluded that the irradiation under the listed conditions caused no significant depolymerization and/or reduction in molecular weight of the chitosan fibers. Accordingly, it can be advantageous to subject chitosan fibers to γ-irradiation in either a presence or an absence of nitrogen plasma.

The chitosan materials have a relatively high nitrogen content. It has been determined that treating such materials in conditions conducive to ionization of nitrogen is especially beneficial in inactivating endotoxin without substantially damaging the chitosan material structure or the efficacy of the chitosan in prompting hemostasis and bioadhesion. More particularly, in some embodiments, chitosan can be subjected to a treatment that increases the quantity of amino groups in and around the chitosan material, so as to inactivate endotoxin and simultaneously increase one or more of wetability, hydrophilicity, and mucoadhesion. In some embodiments, chitosan can be subjected to a treatment that creates nitrogen-based free radicals which can also inactivates endotoxins and simultaneously increases one or more of wetability, hydrophilicity, and mucoadhesion.

In some embodiments, for example, a chitosan material is treated with an ionized nitrogen gas, more specifically a nitrogen-based plasma, preferably under ambient temperature, so as to effectively inactivate endotoxins on chitosan without negatively affecting the efficacy or molecular weight of the chitosan.

Gas plasmas, for example, can be used for sterilization in the food and beverage bottling industries inactivating bacteria, bacterial spores, viruses, fungi, prions and pyrogens. The treatment of chitosan by non-thermal gas plasma technique provides significant advantages over conventional sterilization methods. For example, non-thermal atmospheric nitrogen plasma (NtANP) gas plasmas do not degrade thermolabile chitosan in contrast to electron beam sterilization methods.

In some embodiments, non-thermal atmospheric nitrogen plasma may be the ideal reagent for depyrogenating chitosan since the process not only sterilizes, but increases surface mucoadhesivity by addition of elemental nitrogen to chitosan surfaces. Surface modification of chitosan membranes with an increased incorporation of nitrogen and oxygen groups has been established with $N_2$ plasma treatment. In some embodiments, the surface modification can enhance surface hydrophilicity and bioadhesion. Accordingly, it can be advantageous to subject chitosan fibers to nitrogen plasma in either a presence or an absence of γ-irradiation.

Figure 2:
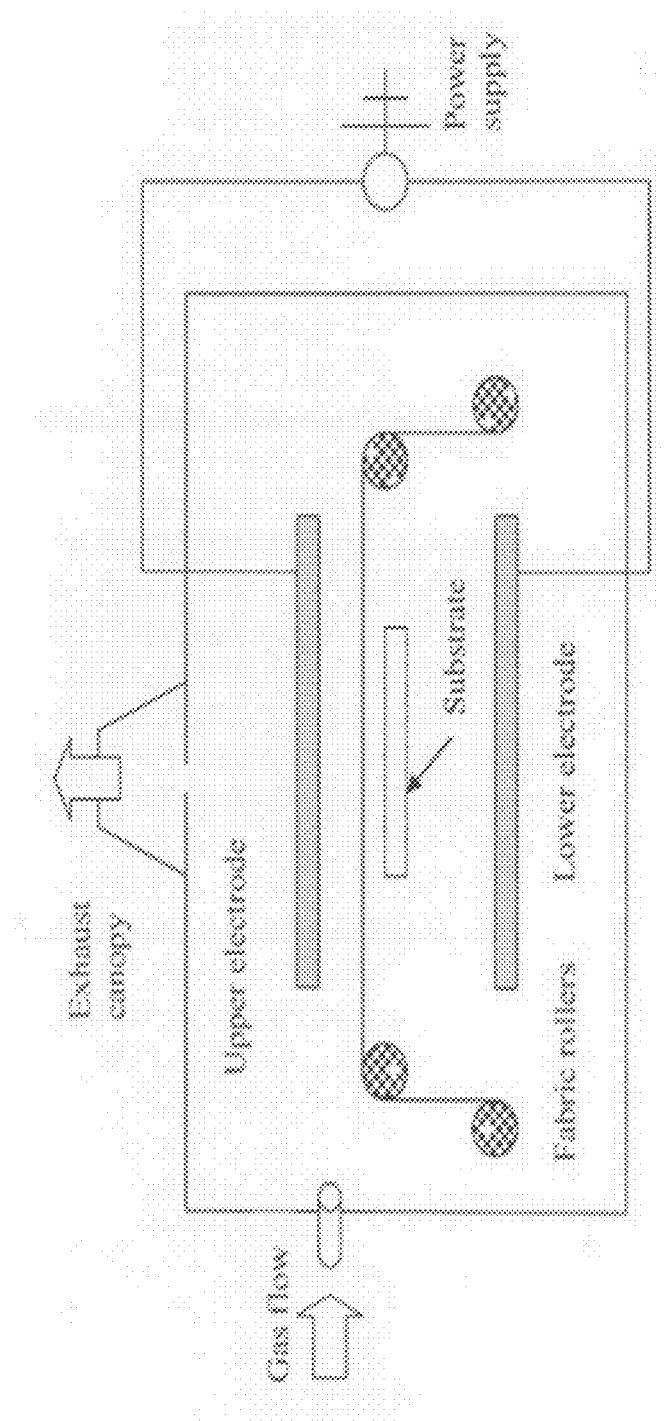
FIG. 2 illustrates a schematic of one embodiment of a North Carolina Atmospheric Plasma System (NCAPS).

FIG. 2 illustrates a schematic of the North Carolina Atmospheric Plasma System (NCAPS) at North Carolina State University which can be utilized to treat chitosan materials. In some embodiments, the nitrogen plasma instrument can be used to treat the chitosan material as described herein.

The schematic of the low temperature nitrogen plasma sterilization illustrated in FIG. 2 shows the simple, high throughput system. Temperature measurements are controlled by a TEFLON® coated thermo-coupler moderated by an analog-to-digital converter. In some embodiments, experimental conditions including time and frequency of plasma exposure and voltage between electrodes can be controlled and varied with this instrument.

In some embodiments, an optimal nitrogen plasma dosimetry can achieve a chitosan with EU levels <20 EU/gm. For example, a "sub-sterilization incremental dose" protocol with variations in power, frequency and plasma exposure time can be applied to our selected chitosan hemostat to allow survival curves to be calculated for residual endotoxin (EU/g) and bacterial bioburdens (Colony Forming Units (CFUs/gm). 50 CFUs and EUs plotted on a log vertical scale and plasma exposure (time power) on the linear horizontal scale enable calculation of the log [N(t)/No]=k.t relationship (No is initial concentration of CFUs/EUs, Nt the concentrations found at given time and power, k is the endotoxin "death rate" constant, t=Time). To reduce the original CFU/EU levels by 90% is one log10. A 6 log10 reduction in EU is necessary to secure adequate endotoxin reduction for implantation.

An example of chitosan endotoxin reduction with nitrogen plasma that has been observed with these techniques is given in Table 2. Conditions used in the laboratory for this nitrogen plasma treatment are as follows: frequency; 1.373 kHz with voltage across the plates at 6.3 kVrms and 7.6 KVmax.

TABLE 2

| Material | EU/gm |
| --- | --- |
| Chitosan/Foreign Source (FS) before plasma | 620.5 |
| *Chitosan FS γ-irrad. + N2 plasma (5 min) | 52.8 |
| **Chitosan FS Fabric γ-irrad. + N2 plasma (10 min) | 12.7 |
| ***Shrimp Lotox Chitosan (powder) (HemCon) | <65 |

*Endotoxin levels were determined by Steri-Pro Labs, Ontario, CA. Endotoxin levels are now determined in Dr. Kirsch's laboratory and crosschecked in the Steri-Pro Labs - see B.4.
**FDA endotoxin requirements for an implantable medical device (20 EU/gm or device).
***Shrimp Lotox ™, "ultrapure chitosan," from Syndegen, Claremont CA (material not available for commercial sale), molecular weight (M.W.) 160-312 kDa.

Table 2 displays chitosan endotoxin levels before and after nitrogen plasma treatment. Chitosan non-woven textile from a foreign source (FS) and previously gamma irradiated were assayed in this experiment.

In some embodiments, when chitosan is treated with nitrogen plasma the effects of nitrogen plasma on chitosan materials have established that despite shallow surface penetration of N2 plasma reactants (NO, OH radicals, N metastables) there are no alterations of hemostatic functional capability.

In some embodiments, plasma treatment can also be carried out using, for example, an e⁻Rio™ atmospheric pressure plasma system APPR-300-13 available from APJeT Inc. The machine uses RF electric fields, 1300 W @ 27 MHz RF/1 mm gap, to produce a unique, non-thermal, glow-discharge plasma that operates at atmospheric pressure with a cooling requirement of 1 gpm @ 20 psi max.

Figure 3:
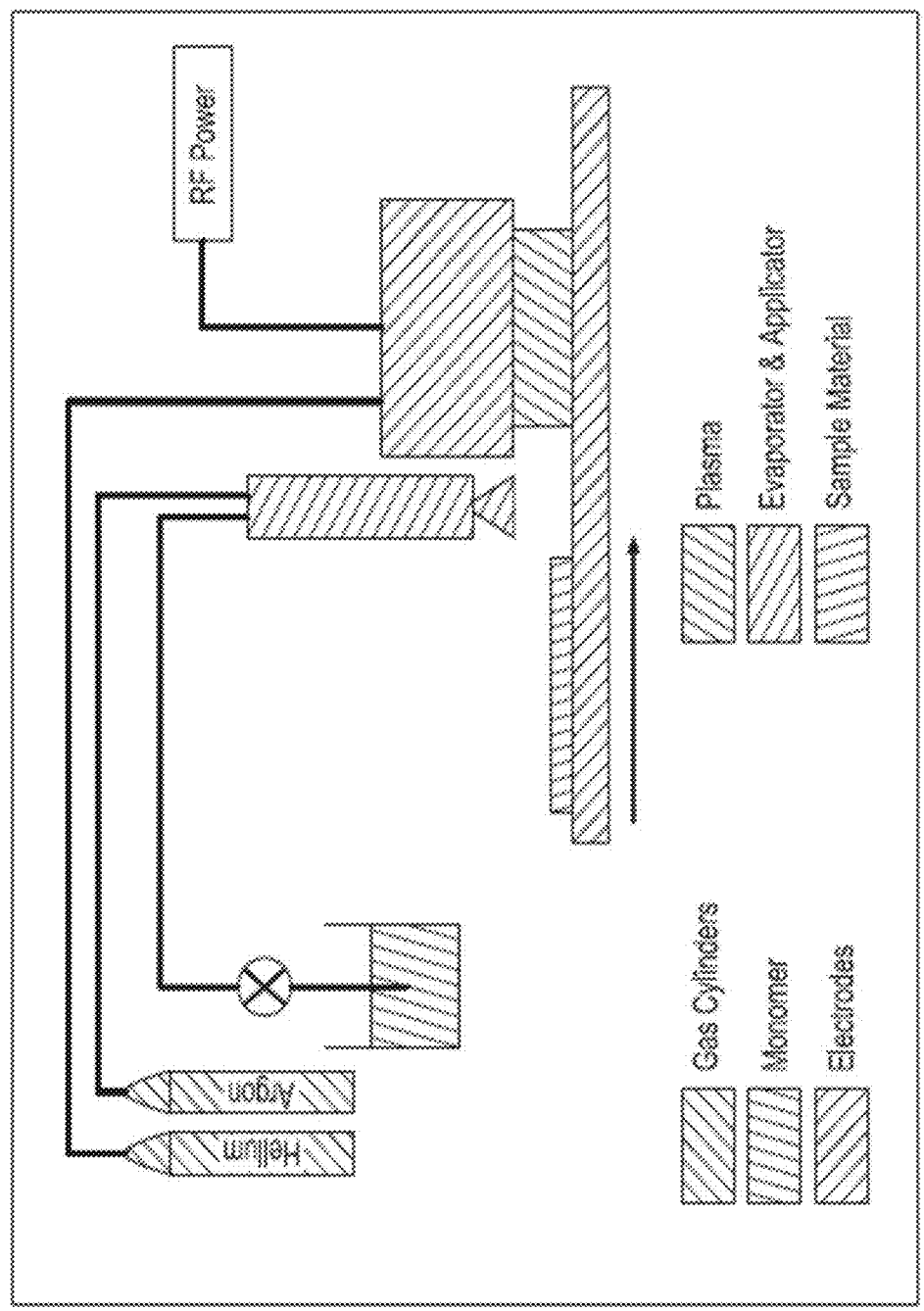
FIG. 3 is a schematic depiction of one embodiment of a plasma treatment assembly.

FIG. 3 is a schematic depiction of one embodiment of a plasma treatment assembly. In some embodiments, the plasma assembly can include an evaporator and applicator.

The evaporator can be a heated assembly that vaporizes a monomer that is to be applied to the chitosan samples. Heat is regulated by a logic controller that is connected to a thermo-coupler attached to the evaporator. The applicator acts as a heated nozzle to apply vaporized monomer to the fibrous chitosan sample. The heat maintains the vapor property of the monomer. Heat preferably is regulated by a logic controller that is connected to a thermo-coupler attached to the applicator.

It is to be understood that multiple methods and assemblies for plasma treatment of chitosan can be employed. For example, chitosan materials can be treated under a nitrogen plasma and then packaged under nitrogen gas. In some embodiments, relatively large quantities of chitosan materials are treated under nitrogen plasma and are then divided into individual doses and packaged separately. In still other embodiments, chitosan can be partially packaged, such as enclosed within a package having an unsealed opening, plasma-treated in the partially packaged condition, and the package may be fully sealed in the plasma treatment zone or a nearby nitrogen field.

In further embodiments, the chitosan material can be packaged prior to plasma treatments. Preferably the chitosan material is sealed in a nitrogen field, and can be prepared substantially as discussed above. In some embodiments, the RF power activates the nitrogen within the packaging, which is believed to create nitrogen-based free radicals that contribute to deactivation of the endotoxin. Of course, it is to be understood that various types and configurations of assemblies and apparatus may be used for the plasma treatment.

Embodiments discussed above have described treating chitosan materials in a nitrogen field involving plasma, γ-irradiation, or the like. In other embodiments, other methods and apparatus that will increase the concentration of amino groups on and around the chitosan can be employed. Preferably such methods additionally provide nitrogen-based free radicals. Such methods may involve other types of irradiation, as well as variations in power, duration, and the like as compared to the examples specifically discussed herein.

In accordance with yet further embodiments, chitosan materials are treated using both plasma and a nitrogen field and γ-irradiation. In some embodiments the chitosan is first treated with γ-irradiation and then treated under the plasma. In other embodiments the order is reversed.

For example, samples of fibrous high molecular weight chitosan having a molecular weight about 700 kDa and a degree of acetylation of about 85% were treated. These samples had been sealed in packages and in a nitrogen field, by first γ-irradiating the packaged samples at a level of 25 Gy, and then plasma treating the still-packaged samples. The treated samples were then subjected to LAL testing. A sample so treated under plasma for about 5 minutes was tested to have 9.6 EU/device, and 52.8 EU/gm based on a 20-fold dilution. A sample so treated under plasma for about 10 minutes was tested to have 2.3 EU/device, and 12.7 EU/gm based on a 20-fold dilution.

In some embodiments described above, chitosan is treated with an acetic acid solution so as to promote adhesion. In further embodiments, chitosan is not treated with acetic acid, and instead is subjected to γ-irradiation in a nitrogen field, nitrogen-gas based plasma treatment, and/or another treatment method that increases the concentration of amino groups on and around the chitosan so as to increase wetability, hydrophilicity and mucoadhesion without exposure to the acetic acid after being formed into a fleece.

It is to be understood that further treatments may enhance hemostatic properties of chitosan-based materials. For example, in one embodiment, chitosan materials are soaked in alcohol, preferably for about an hour. In experiments, such a treatment caused the chitosan materials to be much whiter, but with no structure change of the chitosan fiber. The total bacterial count of the chitosan material was also reduced. Such treated materials can then be further treated using γ-irradiation, plasma, or both.

Various chitosan materials can be subjected to the nitrogen plasma and/or gamma irradiation treatments described herein. Chitosan can be utilized as a hemostat in various compositions and forms. In some embodiments, the form of the chitosan material can have particular advantages that are suitable for different medical purposes, including the use of the chitosan material internal and topical. Examples of various chitosan materials or forms are described herein. For example, FDA-approved topical chitosan hemostats can include lyophilized flakes, granular powder, microfibrillar, high molecular weight chitosan, and microfibrillar, non-woven textiles. In certain embodiments, the chitosan materials for internal and topical use can include chitosan shards, films, ribbons, fibrids, sponges, flakes, slurries, nanoparticulates, gels, solutions, aerosols, and/or other forms of chitosan material as described herein.

Figure 4B:
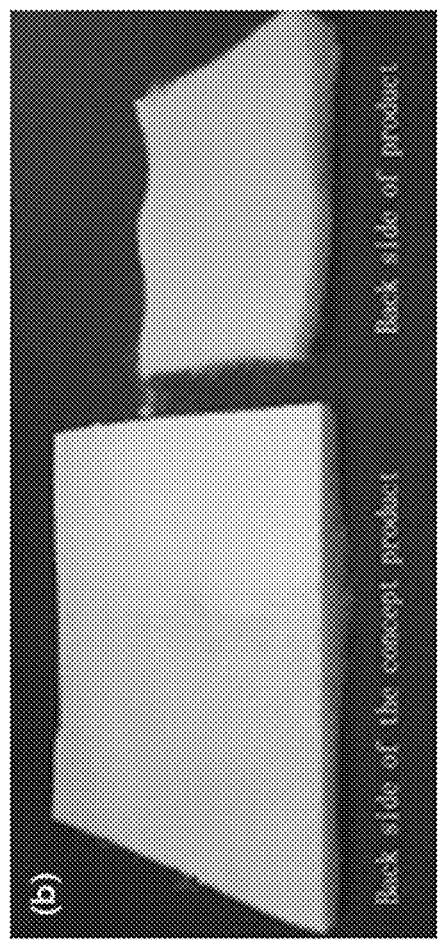
FIGS. 4A-D illustrate embodiments of commercially available "medical-grade" forms of chitosan.
Figure 4A:
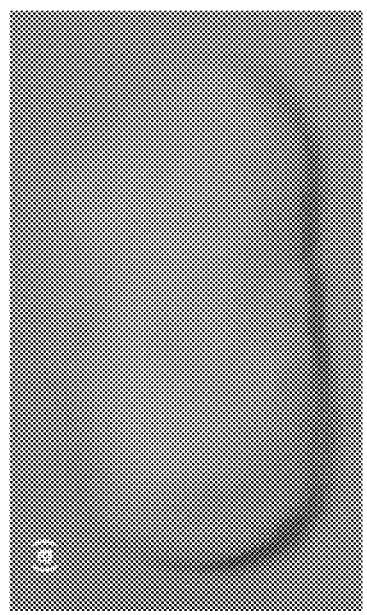
Figure 4D:
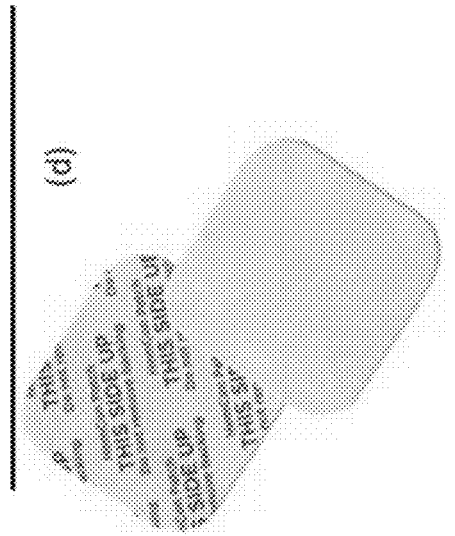
Figure 4C:
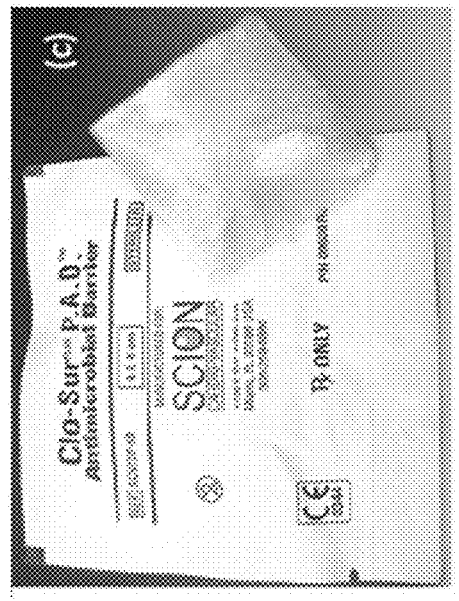

FIGS. 4A-4D illustrate commercially available "medical-grade" forms of chitosan. The medical grade forms of chitosan can vary from fleece alone as in FIG. 4A or fleece compressed into a non-woven fabric or felt as illustrated in FIG. 4B. In some embodiments, the chitosan can be in the form of a lyophilized pads as shown in FIG. 4C. FIG. 4D illustrates a medical grade chitosan in the form of a lyophilized dressing.

In some embodiments, a chitosan fleece can be deployed through endoscopic deployment. The flexibility of materials such as chitosan fleece, non-woven textiles and pads provide ease of deployment through an endoscopic port. In some embodiments, a non-woven fabric or pad can be readily deployed via an endoscopic port whereas a lyophilized product lacks flexibility. In some embodiments, chitosan shards, films, ribbons, fibrids, and/or other forms of chitosan material as described herein can be more readily deployed through an endoscope. Therefore, the choice of chitosan end product will vary depending on the intended use.

In some embodiments, these various chitosan materials can be subjected to the same purification treatments. In some embodiments, the depyrogenation of the chitosan material with nitrogen plasma and gamma irradiation techniques as described herein have proven to achieve acceptable levels of endotoxin purification to be utilized in internal application. For example, the depyrogenated chitosan fleece and/or non-woven fabric or pad material can be delivered through an endoscopic port to a surgical site and used or implanted internally to control bleeding and/or as a drug delivery vehicle.

The hemostatic action of chitosan is based on both tissue bioadhesion and condensation of red blood cells and other formed elements to create a bleeding barrier. Chitosan's glucosamine residues confer a robust surface of positive amine groups binding to tissues' surface negative sialic acid charges. Hypothesized mechanisms for chitosan's bioadhesion are: electronic, adsorptive, wetting, and diffusion. Bioadhesion, whether due to electrostatic, hydrogen bonding, or van der Waals intermolecular interactions creates a hemostatic barrier without activation of the intrinsic or extrinsic coagulation cascade. Chitosan promotes wound healing by activation of macrophages, cytokines, and inhibition of gram-negative bacteria.

The treatment of chitosan materials with nitrogen plasma and gamma irradiation techniques can provide purification of the chitosan material but also the hemostatic advantages as discussed above. Nitrogen plasma acts on the surface of the chitosan material. It has been found that the greater the surface area of the chitosan expose during treatment the more effective and efficient the depyrogenation techniques. In some embodiments, it is advantageous to provide chitosan material with a greater exposed surface area and thereby providing a more readily depyrogenated chitosan material.

The fine structural differences between microfibrillar chitosan fleece and lyophilized chitosan flakes are shown in scanning electron micrographs of FIGS. 5A-D. The microfibrillar chitosan and lyophilized chitosan flakes were studied to determine the effect of plasma mediated surface depyrogenation in comparison to the enhanced surface area of the microfibrillar chitosan.

Figure 5B:
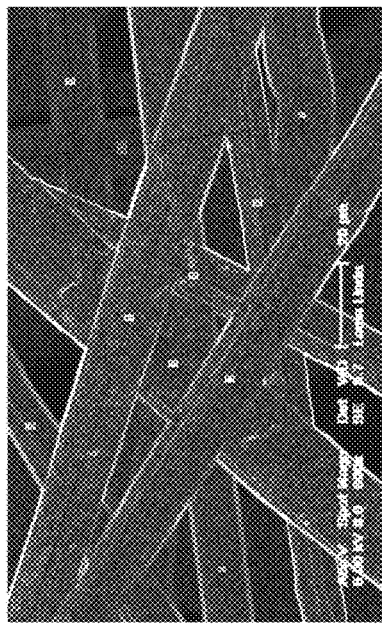
FIGS. 5A-D illustrate Scanning Electron Microscopy (SEM) comparisons of the surface areas for microfibrillar chitosan and a HemCon® lyophilized dressing.
Figure 5D:
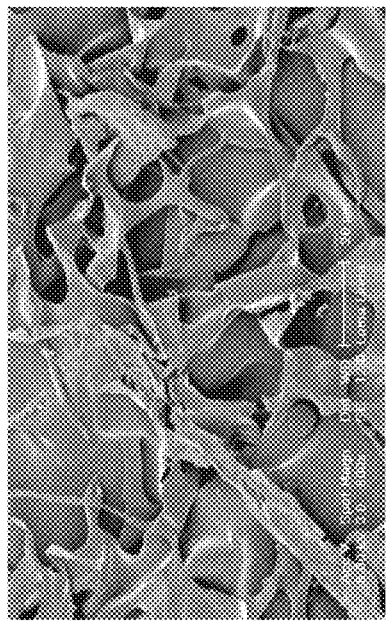
Figure 5A:
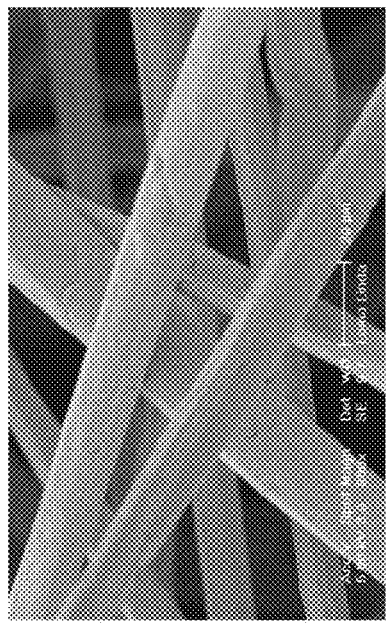
Figure 5C:
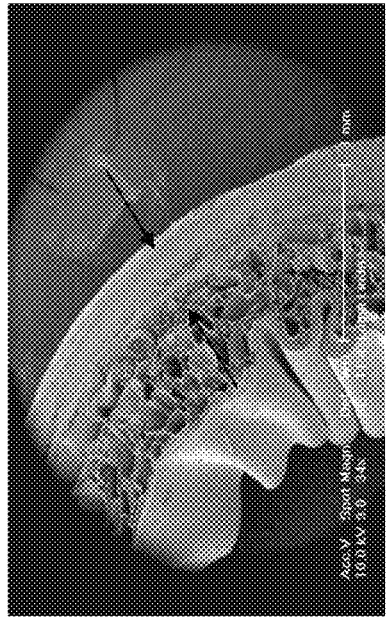

FIGS. 5A-D provide Scanning Electron Microscopy (SEM) images for comparison of the surface areas for microfibrillar chitosan and a HemCon® lyophilized dressing. FIG. 5A shows a SEM of microfibrillar chitosan with a mean diameter of fibers at 16.7±3.6 μm (range 10-26 μm). FIG. 5B shows an edge enhanced image of FIG. 5A, analyzed using ImageJ software. Eleven fibers in the 150×100 μm field of view (FOV) were modeled as cylinders using fiber length and width. The surface area to volume ratio (S/$V_p$) of microfibrillar chitosan is 4.7 nm$^{-1}$, thus having a blood penetration depth of 5 mm. A 1×1×5 mm volume of microfibrillar chitosan presents a surface area of 23.5 μm$^2$ to blood products. The SEM of a HemCon® lyophilized dressing is in FIG. 5C and FIG. 5D. As shown in FIG. 5C, the HemCon® lyophilized dressing exposes a smaller chitosan surface compared to microfibrillar chitosan. Arrows denote the non-stick side of the dressing. To account for the convoluted surface of HemCon® lyophilized dressing, a surface area gain of 50% is assumed and the S/$V_p$ is 4.1 nm$^{-1}$. A 1×1×0.365 mm volume of HemCon® lyophilized dressing presents a surface area of 0.0015 μm$^2$ to blood. The ratio of microfibrillar chitosan surface area to the HemCon® lyophilized dressing in a 1×1 mm patch is 23.5/0.001 or 15,667. The enhanced surface area of microfibrillar chitosan may account for enhanced adhesion, hemostasis, and more effective plasma mediated surface depyrogenation. In some embodiments, it can be effective to increase the surface area of the chitosan material to further enhance the characteristics of the chitosan material, including the effectiveness of depyrogenation techniques.

Chitosan can be pre-treated or specially prepared to increase the effectiveness of nitrogen plasma and gamma irradiation treatment. Because nitrogen plasma can act on the surface of any physical form of chitosan, an increase in surface area to volume ratio can allow for more effective depyrogenation of the chitosan material. In some embodiments, the flexibility required for laparoscopic implantation and internal surgical placement may alter the form of chitosan material used. For example, ultra-thin chitosan materials can be appropriate for laparoscopic implantation due to the durability and flexibility of the material. The extent of depyrogenation of certain forms of chitosan and the required flexibility of the material are characteristics that can direct the shape and/or structure of the chitosan material utilized.

In some embodiments, achieving the targeted endotoxin reduction may require producing and treating ultra-thin chitosan. The thin chitosan material can be easier to purify or depyrogenate with surface active agents such as nitrogen plasma. In some embodiments, with ultra-thin chitosan, full sample penetration or substantially full sample penetration by the nitrogen plasma reactants can be achieved. Additionally, in some embodiments, the ultra-thin chitosan can be a strong and durable material that is flexible and malleable but retains continuity so that it can be moved as a unit and doesn't break apart when manipulated during use.

In some embodiments, the ultra-thin chitosan can be prepared as "excelsior-like" fibrids. Fibrids are short, irregular fibrous shards used in the felt and paper manufacturing industry. Fibrids are manufactured more economically than microfibrils and because of the small dimensions may be more susceptible to both nitrogen plasma depyrogenation and resorption. Chitosan engineering technology and textile expertise is necessary to produce and depyrogenate this ultra-thin chitosan formulation.

The ultra-thin chitosan can be prepared through several methods. In some embodiments, the chitosan can be prepared utilizing methods and techniques as described previously herein with reference to FIG. 1. In some embodiments, chitosan blocks can be formed from physical means or techniques such as compression. In some embodiments, the chitosan blocks can be created by utilizing large chitosan flakes directly obtained from shellfish with multi centimeter dimensions. The chitosan flakes can be plasticized with aqueous organic acids, such as acetic or lactic acid. The chitosan flakes are then compressed and consolidated under vacuum to a density greater than 0.6 g/cm$^3$. This treatment will form chitosan blocks for processing.

In some embodiments, the chitosan blocks can be shredded to shards with specific dimensions of width and thickness. The shredded shards manufacturing process can be analogous to the manufacture of cellulose "wood wool" or excelsior used as "Easter basket grass." Chitosan shard formulation produced through this method can form chitosan material with an increased surface area than that of chitosan microfibrils.

In some embodiments, the increased surface area can produce a chitosan material that can be potentially more vulnerable to nitrogen depyrogenation and resorption. In some embodiments, the chitosan shard formation can be amenable to laparoscopic implantation for internal medical purposes. In some embodiments, the chitosan shard formation formed by the shredded shard manufacturing process can have the necessary flexibility and rigidity for internal medical applications.

The width and the thickness can be varied to produce shards for different sizes and shards ideal for further processing. In some embodiments, the chitosan excelsior or shard can be superfine. The chitosan excelsior or shard can have dimensions of 0.15 mm (0.006 inch) strand thickness and 0.5 mm (0.020 inch) width. In some embodiments, the chitosan shard thickness can be from about 1 μm to 5 μm to about 50 μm, 100 μm, 200 μm, or 250 μm; however, thicker or thinner shards can also be advantageously provided in other embodiments. In some embodiments, the chitosan shard strand width can be greater than or equal to about 0.35 mm or less than or equal to about 0.65 mm. In certain embodiments, the strand width can be from about 0.35 mm, 0.4 mm, or 0.45 mm to about 0.5 mm, 0.55 mm, 0.6 mm, or 0.65 mm; however, wider or narrower shards can also be advantageously provided in other embodiments. Preferably the fibrids have a substantially longer length than width, e.g., a length two times the width, five times the width, ten times the width, or 50 times the width or more.

In certain embodiments, the chitosan materials can be formed through other methods to increase the strength or depyrogenation of the material. The materials can be made from compressed chitosan flakes and/or flake-based chitosan shards. For example, at least two other approaches can be taken to produce an excelsior-like chitosan. In some embodiments, a pulp-like fibrid can be made by the shear induced precipitation of a chitosan solution. The shear induced precipitation can be accomplished by dripping a dilute solution into a stirred coagulant. The solution can be stirred by a shear disc.

In some embodiments, the ultra-thin chitosan can be formed by slitting chitosan film into narrow strips. The term "ultra-thin" as used herein is a broad term, and is to be given its ordinary and customary meaning to a person of ordinary skill in the art (and is not to be limited to a special or customized meaning), and refers without limitation to thicknesses of 0.5 mm or less. The term "narrow strips" as used herein is a broad term, and is to be given its ordinary and customary meaning to a person of ordinary skill in the art (and is not to be limited to a special or customized meaning), and refers without limitation to widths of 1 mm or less. The narrow strips can be of a predetermined dimension. The strips can be of uniform size or the size can be varied. In some embodiments, the narrow strips can be 1 mm wide, 0.5 mm thick and up to 5 cm long. In some embodiments, the chitosan strip width can be greater than or equal to about 0.5 mm or less than or equal to about 1.5 mm. In certain embodiments, the strip width can be about 0.5 mm, 0.75 mm, 1.0 mm, 1.25 mm, and 1.5 mm. In some embodiments, the chitosan strip thickness can be greater than or equal to about 1 μm or less than or equal to about 200 μm. In certain embodiments, the strip thickness can be about 1 μm, 5 μm, 25 μm, 50 μm, 100 μm, 200 μm, or 250 μm. In some embodiments, the chitosan strip length can be greater than or equal to about 1 cm or less than or equal to about 5 cm. In certain embodiments, the strip length can be about 1 cm, 2 cm, 3 cm, 4 cm, and 5 cm.

Several physical forms of a chitosan dressing are available for depyrogenation and endoscopic deployment. In some embodiments, it is necessary to identify an optimal chitosan form compatible with implantation via a laparoscopic port. For example, if the optimal form is a non-woven material that can be furled and unfurled through an endoscope, chitosan textile with shards and/or fibrids can be constructed. For example, in some embodiments, the chitosan textile can be produced by the production of shards from compressed chitosan blocks as described herein. The manufacture of chitosan shards from a compressed chitosan block is a method for producing a chitosan non-woven textile that may be more readily depyrogenated due to the increase in exposed surface area of the shard material. In some embodiments, the production of chitosan shards and/or fibrids can be desirable because of their increased ability to be resorbed after implantation.

Figure 6B:
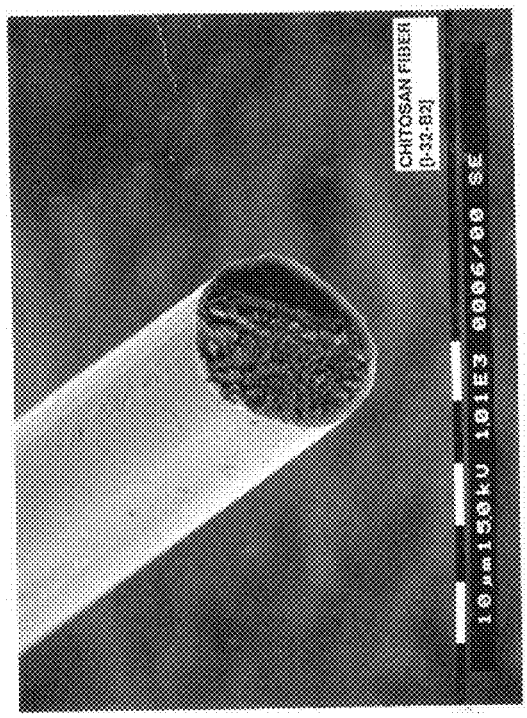
FIG. 6B illustrates an embodiment of a conventional wet spun chitosan filament.
Figure 6A:
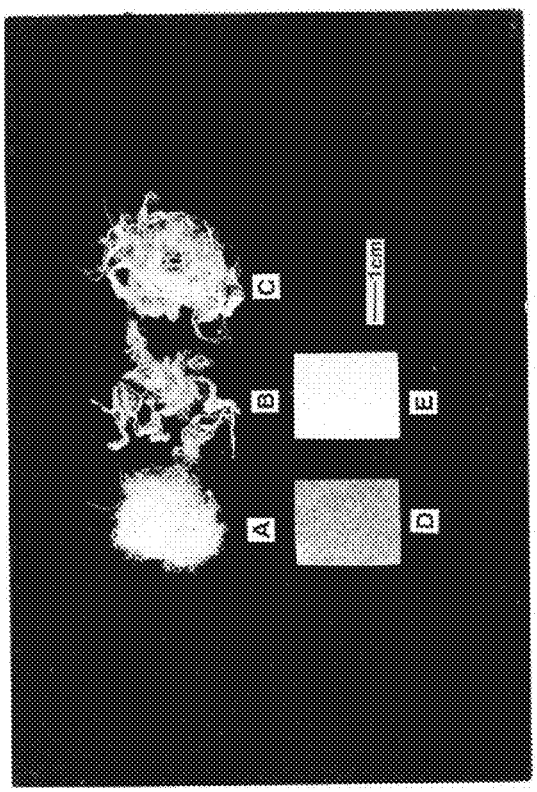
FIG. 6A illustrates embodiments of solution processed chitosan fibrids, including Materials "A", "B", "C", "D", and "E".

FIG. 6A illustrates embodiments of solution processed chitosan fibrids. The chitosan fibrids can have different appearances and different configurations depending on the solution used to process the fibrids. Chitosan fibrids can be processed in varying processing methods including direct shear precipitation, water processing, alcohol processing, and/or other processing methods known in the art. The different chitosan fibrid end-products of the varying processing solutions are shown in FIG. 6A(a)-6A(e). The embodiments shown in FIG. 6A(a) are chitosan fibrids made by direct shear precipitation. Water processed fibrids have the appearance of the thin narrow strips as shown in FIG. 6A(b). The water processed fibrids of FIG. 6A(b) can be formed into a thin paper-like sheet structure as shown in FIG. 6A(d). FIG. 6A(c) shows alcohol processed and FIG. 6A(e) shows the paper-like sheet obtained from the fibrids of FIG. 6A(c). FIG. 6B illustrates a conventional wet spun chitosan filament. The white scale bar depicted in FIG. 6B represents 10 microns.

In some embodiments, the thin paper-like sheet can be utilized as an end product for internal and/or external purposes to promote wound healing and/or to act as a vehicle for drug delivery. In other embodiments, the thin paper-like sheets can be combined with other sheets of the same chitosan fibrid material and/or different material to form a thicker end product including a network of chitosan fibrids. However, in other embodiments, a thicker end product can be made by making a network of chitosan fibrids, chitosan shards, or a combination of both. In some embodiments, the network of ultra-thin chitosan can include a fleece-like, fabric-like, and/or assembly of chitosan shards, films, ribbons, fibrids, and/or other forms of chitosan material as described herein. Additionally, the chitosan end product can contain medicinal agents and/or other active agents to assist in wound healing or drug delivery as described in detail herein. In some embodiments, similar to chitosan of fibrous materials, the chitosan fibrids can also be constructed as a textile in a puff, fleece, fabric or sheet form.

Embodiments of a chitosan-based hemostatic textile can be provided in many forms depending upon the nature of the wound and the treatment method employed. For example, a puff, fleece, or sponge form can be preferable for controlling active bleeding from an artery or vein, or for internal bleeding during laparoscopic procedures. In neurosurgery, where oozing brain wounds are commonly encountered, a flexible sheet form of the hemostatic material can be preferred. Likewise, in oncological surgery, especially of the liver, it can be preferred to employ a sheet form or sponge form of the hemostatic material, which is placed in or on the tumor bed to control oozing. In dermatological applications, a sheet form can be preferred. In closing punctures in a blood vessel, a puff form is generally preferred. A suture form, such as a microsuture or a macrosuture, can be preferred in certain applications. In performing a laparoscopic partial nephrectomy a chitosan sponge, shard, fibrid, and/or films can be applied to the surgical site. In some embodiments, the network of chitosan shards and/or fibrids need not be processed into a specific textile, but instead can be packed, clumped, or wadded together into a network of ribbons that resembles Easter basket grass. The packed, clumped, or wadded together network of ribbons can be formed into any desired size.

In some embodiments, embodiments of chitosan are amenable to all of these applications and configurations, and embodiments are envisioned in which devices made from such chitosan are formed and shaped accordingly.

In some embodiments, the production of chitosan materials and associated processing can use chitosan of relatively high molecular weight. Such high molecular weight chitosan can be amenable to formation into a fleece that can be formed into a strong and durable material that is flexible and malleable but retains continuity so that it can be moved as a unit and doesn't break apart when manipulated during use.

Figure 7:
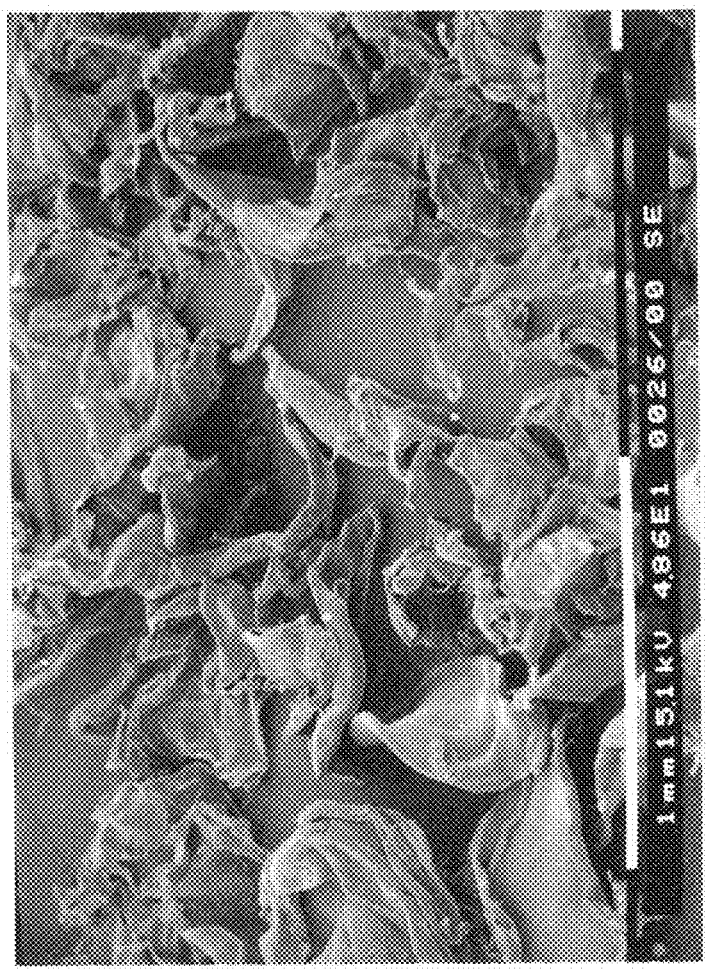
FIG. 7 illustrates an SEM image of an embodiment of chitosan fibrids that are directly obtained by shear induced precipitation of chitosan from solution as shown in Material "A" of FIG. 6A.

FIG. 7 illustrates chitosan fibrids that are directly obtained by shear induced precipitation of chitosan from solution as shown in FIG. 6A(a). The scale bar in FIG. 7 represents 1 mm. The chitosan fibrids as shown in FIG. 7 illustrate the size and exposed surface area of the chitosan fibrid material. The chitosan fibrid material is thinner than the chitosan fibers produced by conventional wet spinning methods and contain a larger exposed surface area. Due to these features, the ultra-thin chitosan material can be more readily depyrogenated with surface acting agents such as nitrogen plasma treatment and gamma irradiation. In some embodiments, the ultra-thin chitosan can be depyrogenated to allow for endotoxin reduction to levels acceptable for internal medical applications while maintaining the hemostatic and mucoadhesion properties of other chitosan materials.

Figure 8B:
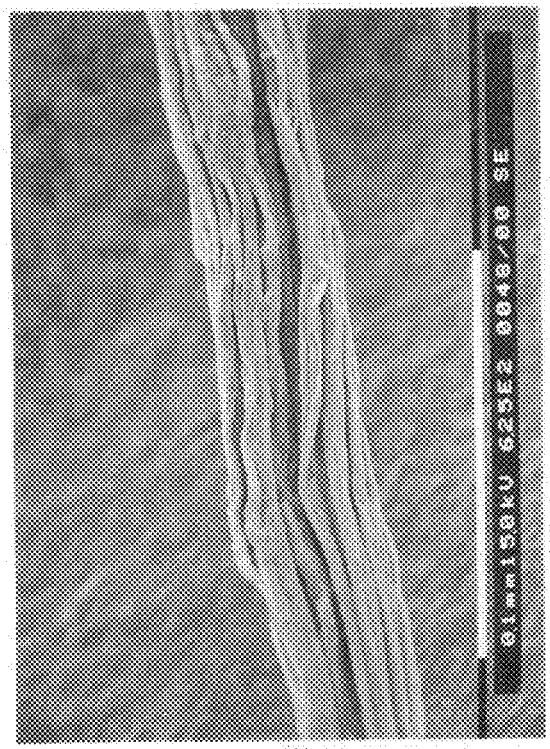
FIG. 8A-B illustrates SEM images of individual chitosan fibrid pulp obtained by the direct precipitation of sheared chitosan solutions.
Figure 8A:
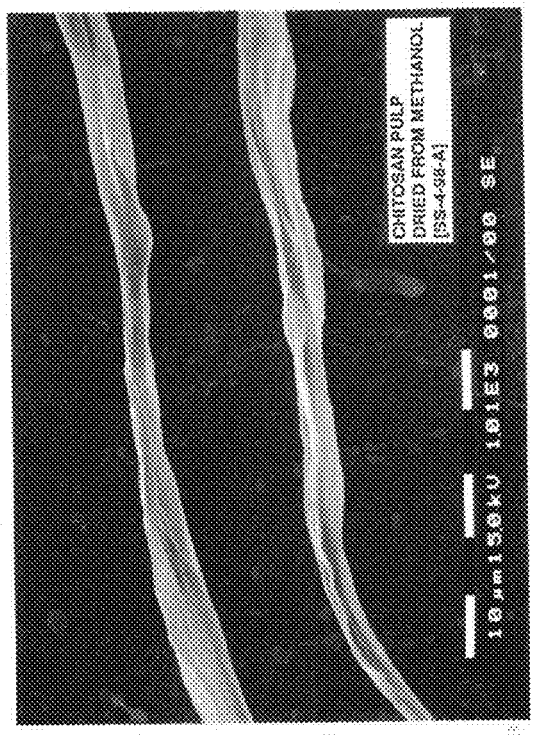

FIG. 8A-B illustrates SEM images of individual chitosan fibrid pulp obtained by the direct precipitation of sheared chitosan solutions. The fibrid pulp exhibit the increased surface area similar to that of chitosan fibrids described with reference to FIG. 7.

Figure 9B:
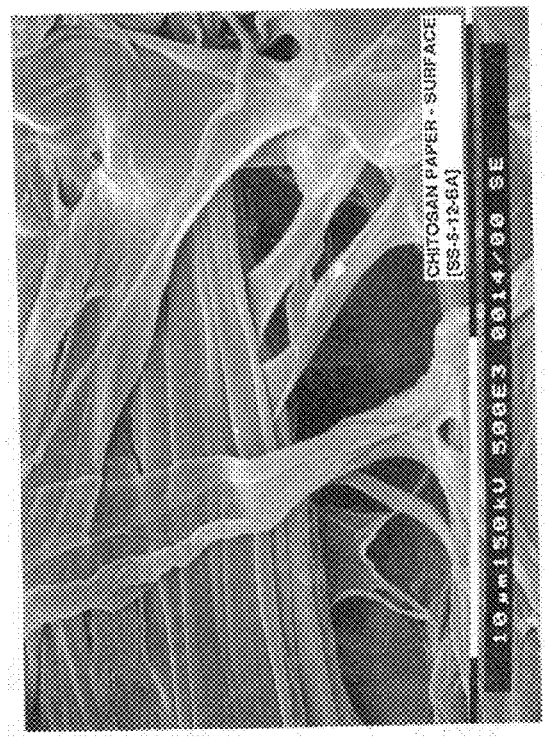
FIG. 9B illustrates an SEM image of a film or paper-like structure obtained from chitosan fibrids.
Figure 9A:
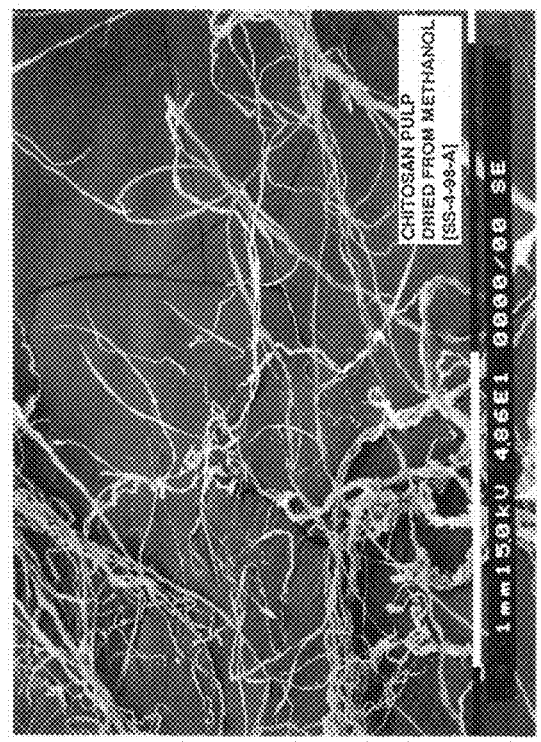
FIG. 9A illustrates an SEM image of chitosan fibrids processed with methanol and obtained from shear precipitated chitosan solution.

FIG. 9A-B illustrates SEM images of chitosan fibrids. FIG. 9A illustrates an SEM image of chitosan fibrids processed with methanol and obtained from shear precipitated chitosan solution. The scale bar represents 1 mm. The chitosan fibrids can be formed into films or paper-like structures. In some embodiments, the films or paper-like structures can be used for topical or internal medical applications as a hemostat and/or drug delivery vehicle. FIG. 9B shows film or paper-like structure obtained from chitosan fibrids. The scale bar represents 10 microns. In some embodiments, the films or paper-like structure can be arranged in a layered configuration to form a larger or thicker chitosan material. In some embodiments, the chitosan fibrid material can include a medicament or other agents that assist in wound healing and/or medicaments or agents that are to be delivered to the target implantation site.

The type of chitosan material formed from chitosan fibrids, shards, films, and/or ribbons will be determined by the intended use. Chitosan fibrids, shards, films, and/or ribbons can be formed into various materials such as a chitosan puff, fleece, film, or sheet similar to chitosan microfibers. In some embodiments, the chitosan fibrid, shards, films, and/or ribbons materials can have lower endotoxin levels than achieved utilizing chitosan microfibers because of the increased surface area exposed to the purification and treatment techniques of nitrogen plasma and gamma irradiation treatment as described herein.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' including but not limited to,' or the like; the term 'comprising' as used herein is synonymous with 'including,' containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' preferred, "desired," or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A method of making a material comprising:
   plasticizing chitosan flakes with an aqueous organic acid;
   physically compressing and consolidating the plasticized chitosan flakes under vacuum into a block;
   shredding or slitting the block into chitosan shards, wherein the chitosan shards have a thickness of from 1 μm to 250 μm, a width of from 0.35 mm to 0.65 mm, and a length two times the width or more; and
   subjecting the chitosan shards to γ-irradiation under a nitrogen plasma.

2. The method of claim 1, wherein the chitosan flakes are of multi centimeter dimensions and are directly obtained from shellfish.

3. The method of claim 1, wherein the chitosan shards are 0.15 mm thick and 0.5 mm wide.

4. The method of claim 1, further comprising processing the chitosan shards into a hemostatic device comprising a network of the chitosan shards.

5. The method of claim 1, further comprising processing the chitosan shards into a drug delivery device comprising a network of the chitosan shards.

6. The method of claim 1, additionally comprising soaking the chitosan shards in an alcohol prior to said subjecting to γ-irradiation under nitrogen plasma.

7. The method of claim 1, wherein said compressing and consolidating under vacuum comprises physically compressing and consolidating the flakes to a density greater than 0.6 g/cm$^3$.

8. A method of making a material comprising:
   plasticizing chitosan flakes with an aqueous organic acid;
   physically compressing and consolidating the plasticized chitosan flakes under vacuum into a block;
   shredding or slitting the block into narrow strips of chitosan material, wherein the narrow strips of chitosan material have a thickness of from 1 μm to 250 μm, a width of from 0.5 mm to 1.5 mm, and a length of 1 cm to 5 cm; and
   subjecting the narrow strips of chitosan material to γ-irradiation under a nitrogen plasma.

9. The method of claim 8, wherein the chitosan flakes are of multi centimeter dimensions and are directly obtained from shellfish.

10. The method of claim 8, wherein the narrow strips of chitosan material are 0.15 mm thick and 0.5 mm wide.

11. The method of claim 8, further comprising processing the narrow strips of chitosan material into a hemostatic device comprising a network of the narrow strips of chitosan material.

12. The method of claim 8, further comprising processing the narrow strips of chitosan material into a drug delivery device comprising a network of the narrow strips of chitosan material.

13. The method of claim 8, additionally comprising soaking the narrow strips of chitosan material in an alcohol prior to said subjecting to γ-irradiation under nitrogen plasma.

14. The method of claim 8, wherein said compressing and consolidating under vacuum comprises physically compressing and consolidating the flakes to a density greater than 0.6 g/cm$^3$.

* * * * *